United States Patent [19]

Haga et al.

[11] Patent Number: 4,755,215
[45] Date of Patent: Jul. 5, 1988

[54] BENZOTRIAZOLES, AND THEIR PRODUCTION AND USE

[75] Inventors: Toru Haga, Takarazuka; Eiki Nagano, Nishinomiya; Ryo Sato; Kouichi Morita, both of Toyonaka, all of Japan

[73] Assignee: Sumitomo Chemical Company, Limited, Osaka, Japan

[21] Appl. No.: 818,812

[22] Filed: Jan. 14, 1986

[30] Foreign Application Priority Data

Jan. 14, 1985 [JP] Japan .................................. 60-004379

[51] Int. Cl.⁴ .................... A01N 43/38; A01N 43/707; C07D 403/04
[52] U.S. Cl. .......................................... 71/92; 71/95; 71/96; 548/257; 548/260; 548/261; 548/476; 548/477
[58] Field of Search ............... 548/257, 260, 261, 476, 548/477; 514/417, 359; 71/92, 95, 96

[56] References Cited

U.S. PATENT DOCUMENTS

| | | | |
|---|---|---|---|
| 4,001,272 | 1/1977 | Goddard | 71/96 |
| 4,240,822 | 12/1980 | Diehl et al. | 71/92 |
| 4,670,042 | 6/1987 | Haga | 548/476 |

FOREIGN PATENT DOCUMENTS 108766   6/1984  Japan .................................. 548/476

OTHER PUBLICATIONS

Journal of the American Chem. Society, "Aromatic Fluorine Compounds II. 1,2,4,5-Tetrafluorobenzene and Related Compounds", 73, (1951), pp. 145-149, by Finger et al.

Journal of the American Chem. Society, "Aromatic Fluorine Compounds. VI. Displacement of Aryl Fluorine in Diazonium Salts", 78 (1956), pp. 2593-2596, by Finger et al.

Primary Examiner—Donald G. Daus
Assistant Examiner—Mark W. Noel
Attorney, Agent, or Firm—Birch, Stewart, Kolasch & Birch

[57] ABSTRACT

A compound of the formula:

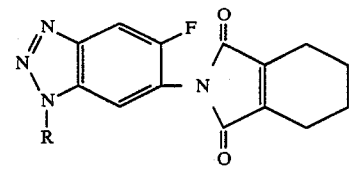

wherein R is a $C_1$-$C_5$ alkyl group, a $C_3$-$C_5$ alkenyl group, a $C_3$-$C_5$ alkynyl group or a $C_3$-$C_7$ cycloalkyl group, which is useful as a herbicide.

11 Claims, No Drawings

BENZOTRIAZOLES, AND THEIR PRODUCTION AND USE

This invention relates to benzotriazoles, and their production and use. More particularly, the present invention relates to novel benzotriazoles, a process for producing them, and their use as herbicides.

Some benzotriazole derivatives (e.g. 4-nitro-1-cyclohexyl-1H-benzotriazole) are known to be effective as herbicides [U.S. Pat. No. 4,240,822]. However, their herbicidal activity is not necessarily satisfactory.

It has now been found that the benzotriazoles of the formula:

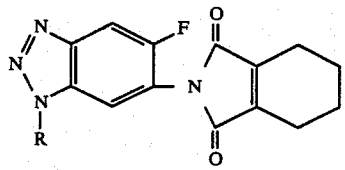

(I)

wherein R is a $C_1-C_5$ alkyl group, a $C_3-C_5$ alkenyl group, a $C_3-C_5$ alkynyl group or a $C_3-C_7$ cycloalkyl group exhibit a high herbicidal activity against a wide variety of weeds including broad-leaved weeds, Graminaceous weeds and Cyperaceous weeds in agricultural plowed fields by foliar or soil treatment without producing any material phytotoxicity on various agricultural crops such as corn, wheat, rice and soybean. Examples of the broad-leaved weeds are wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), cleavers (*Galium aparine*), tall morningglory (*Pharbitis purpurea*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annula bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), etc. Examples of the Cyperaceous weeds are rice flatsedge (*Cyperus iria*), purple nutsedge (*Cyperus rotundus*), etc.

The benzotriazoles (I) of the present invention are also effective in exterminating paddy field weeds including Graminaceous weeds such as barnyardgrass (*Echinochloa oryzicola*), broad-leaved weed such as common falsepimpernel (*Lindernia procumbens*), indian toothcup (*Rotala indica*) and waterwort (*Elatine triandra*), Cyperaceous weeds such as umbrella sedge (*Cyperus difformis*) and needle spikerush (*Eleocharis acicularis*) and others such as monochoria (*Monochoria vaginalis*) and arrowhead (*Sagittaria pygmaea*) without producing any phytotoxicity to rice plants on flooding treatment.

In the above formula (I), the term "$C_1-C_5$ alkyl group" covers methyl, ethyl, n-propyl, isopropyl, n-butyl, isobutyl, sec-butyl, n-pentyl, etc. The term "$C_3-C_5$ alkenyl group" includes allyl, crotyl group, methallyl, etc. The term "$C_3-C_5$ alkynyl group" includes propargyl, 2-butynyl, 3-butynyl, 2-pentynyl, 3-pentynyl, etc. Examples of the term "$C_3-C_7$ cycloalkyl group" are cyclopropyl, cyclobutyl, cyclopentyl, cyclohexyl, cycloheptyl, etc. Among them, preferred are those wherein R is a $C_3-C_5$ alkenyl group or a $C_3-C_5$ alkynyl group. Typical examples of the preferred compounds are 2-[5-fluoro-1-(2-propynyl)benzotriazol-6-yl]-4,5,6,7-tetrahydro-2H-isoindole-1,3-dione, and 2-[5-fluoro-1-(2-propenyl)benzotriazol-6-yl]-4,5,6,7-tetrahydro-2H-isoindole-1,3-dione.

The benzotriazoles (I) of the invention are obtained by reacting an aniline of the formula:

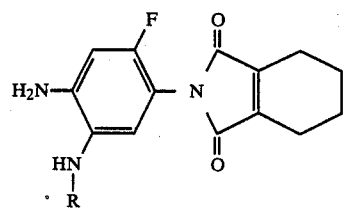

(II)

wherein R is as defined above with a nitrite or nitrous ester in an inert solvent in the presence of an aqueous acid at a temperature of 0° to 50° C. for a period of 5 minutes to 4 hours.

The nitrite or nitrous ester may be used in an amount of about 1 to 2 equivalents to the aniline (II). Also, the acid may be used in an amount of about 1 equivalent to a large excess to the aniline (II).

As the nitrite or nitrous ester, there may be used sodium nitrite, potassium nitrite, isoamyl nitrite, etc. Examples of the acid are hydrochloric acid, sulfuric acid, acetic acid, etc. Examples of the inert solvent are ethers (e.g. dioxane, tetrahydrofuran), aliphatic acids (e.g. formic acid, acetic acid), water, etc. Their mixtures are also usable.

After completion of the reaction, the reaction mixture is subjected to an ordinary post-treatment such as extraction with an organic solvent and concentration. If desired, any conventional purification procedure such as chromatography or recrystallization may be adopted.

A typical example for production of the benzotriazoles (I) is illustratively shown below.

EXAMPLE 1

2-[4-Amino-2-fluoro-5-(2-propynylamino)phenyl]-4,5,6,7-tetrahydro-2H-isoindole-1,3-dione (0.59 g) was dissolved in acetic acid (1.9 ml), and sodium nitrite (0.13 g) was added thereto at a temperature of 10° to 15° C. After stirring for 10 minutes, the reaction mixture was admixed with water and extracted with ethyl acetate. The extract was washed with water and an aqueous solution of sodium bicarbonate, dried and concentrated. The residue was purified by silica gel thin layer chromatography using a mixture of ethyl acetate and hexane (1:2 by volume) as an eluent to give 2-[5-fluoro-1-(2-propynyl)benzotriazol-6-yl]-4,5,6,7-tetrahydro-2H-isoindole-1,3-dione (0.07 g) as a resinous material.

$^1$HNMR (CDCl$_3$, δ): 1.80 (br, 4H), 2.41 (br, 4H), 2.50 (t, 1H, J=2.6 Hz), 5.34 (d, 2H, J=2.6 Hz), 7.56 (d, 1H, J=6.0 Hz), 7.73 (d, 1H, J=9.0 Hz).

Some examples of the benzotriazoles (I) produced in the same manner as above are shown in Table 1.

TABLE 1

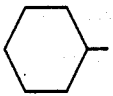

| Compound No. | R | State | ¹HNMR (CDCl₃, δ) |
|---|---|---|---|
| 1 | HC≡C—CH₂— | resinous | 1.80 (br, 4H), 2.41 (br, 4H), 2.50 (t, 1H, J=2.6 Hz), 5.34 (d, 2H, J=2.6 Hz), 7.56 (d, 1H, J=6.0 Hz), 7.73 (d, 1H, J=9.0 Hz) |
| 2 | cyclohexyl | resinous | 1.50 (br, 10H), 1.80 (br, 4H), 2.41 (br, 4H), 4.55 (m, 1H), 7.43 (d, 1H, J=6.0 Hz), 7.73 (d, 1H, J=9.0 Hz) |
| 3 | CH₃CH₂CH₂— | resinous | 0.98 (t, 3H, J=7.6 Hz), 1.19 (m, 2H), 1.85 (br, 4H), 2.45 (br, 4H), 4.54 (t, 2H, J=7.6 Hz), 7.41 (d, 1H, J=6.0 Hz), 7.77 (d, 1H, J=9.0 Hz) |
| 4 | H₂C=CH—CH₂— | resinous | 1.82 (br, 4H), 2.43 (br, 4H), 5.1–5.4 (m, 4H), 5.7–6.4 (m, 1H), 7.38 (d, 1H, J=6.0 Hz), 7.74 (d, 1H, J=9.0 Hz) |
| 5 | (CH₃)₂CH— | resinous | 1.63 (d, 6H, J=6.6 Hz), 1.85 (br, 4H), 2.45 (br, 4H), 7.35 (br, 1H), 7.47 (d, 1H, J=6.0 Hz), 8.12 (d, 1H, J=9.0 Hz) |

The aniline (II) as the starting material in the process of this invention may be produced according to the following scheme:

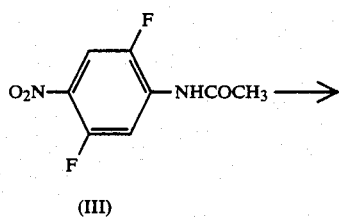

(III)

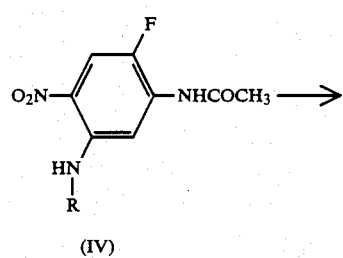

(IV)

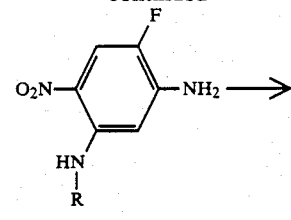

(V)

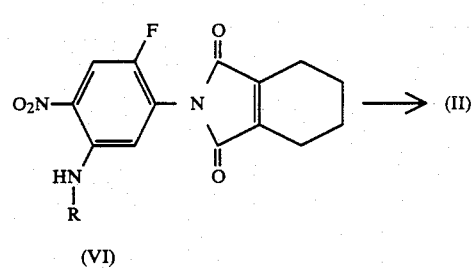

(VI)

wherein R is as defined above.

Explaining the reaction at each step in the above scheme, the starting fluoro-acetanilide (III), i.e. 2,5-difluoro-4-nitroacetoanilide, is known per se [Finger et al.] J. Am. Chem. Soc., 73, 145 (1951); ibid, 78, 2593 (1956), and this is first reacted with 2 equivalents to large excess of an amine of the formula:

R—NH₂       (VII)

wherein R is as defined above in an inert solvent (e.g. dioxane, tetrahydrofuran, ethylene glycol dimethyl ether) at a temperature of 50° to 150° C. for a period of 1 to 24 hours to give the amino-acetanilide (IV). Recovery of the aminoacetanilide (IV) can be accomplished by adding water to the reaction mixture, extracting the resultant mixture with an organic solvent and concentrating the extract. When desired, any purification procedure such as chromatography or recrystallization may be applied.

The amino-acetanilide (IV) is reacted with 2 equivalents to a large excess of a mineral acid (e.g. hydrochloric acid, hydrobromic acid) in an inert solvent (e.g. methanol, ethanol, dioxane, water) at a temperature of 20° to 100° C. for a priod of 1 to 24 hours to give the nitroaniline (V). For recovery of the nitroaniline (V), the reaction mixture is distilled under reduced pressure to remove the mineral acid and the solvent, water is added to the residue, and the resultant mixture is neutralized with an alkali, followed by an ordinary post-treatment such as solvent extraction and concentration. If desired, any conventional purification procedure such as chromatography or recrystallization may be applied.

Then, the nitroaniline (V) is reacted with 1.0 to 1.1 equivalents of 3,4,5,6-tetrahydrophthalic anhydride in an inert solvent at a temperature of 100° to 200° C. for a period of 1 to 48 hours to give the nitrobenzene (VI). As the inert solvent, there may be employed aromatic hydrocarbons (e.g. xylene), halogenated hydrocarbons (e.g. chlorobenzene, dichlorobenzene), aliphatic acids (e.g. acetic acid, propionic acid, butyric acid), water or their mixtures. The nitrobenzene (VI) may be recovered from the reaction mixture by adding water thereto, extracting the resultant mixture with an organic solvent and concentrating the extract. When desired, any purification procedure such as chromatography or recrystallization may be applied thereto.

The nitrobenzene (VI) is then reacted with 3 to 30 equivalents of iron powder in the presence of an aqueous acid (e.g. acetic acid, propionic acid) at a temperature of 60° to 150° C. for a period of 1 to 24 hours to give the aniline (II). As an auxiliary solvent, the reaction system may optionally include ethyl acetate or the like. Recovery of the aniline (II) from the reaction mixture may be carried out by extraction with an organic solvent and concentration, if necessary, followed by purification such as chromatography or recrystallization.

Some typical examples for preparation of the starting compounds are set forth below.

EXAMPLE 2

Production of the amino-acetanilide (IV)

2,5-Difluoro-4-nitroacetanilide (3.0 g) was dissolved in dioxane (14 ml), and propargylamine (2.0 g) was added thereto, followed by heating under reflux for 2 hours. The reaction mixture was allowed to cool, admixed with water and extracted with ethyl acetate. The extract was washed with water, dried and concentrated to give 2-fluoro-4-nitro-5-(2-propynyl)aminoacetanilide (1.1 g). m.p., 216°–217° C.

In the same manner as above, the aminoacetanilides (IV) as shown in Table 2 could be produced:

TABLE 2

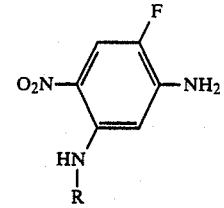

(IV)

| R | Physical property |
|---|---|
| —CH$_2$(CH$_3$)$_2$ | m.p., 146.0–147.0° C. |
| —CH$_2$CH$_2$CH$_3$ | m.p., 138.5–139.0° C. |
| —CH$_2$CH=CH$_2$ | m.p., 155.6° C. |
| —CH$_2$C≡CH | m.p., 216–217° C. |
| —⟨H⟩ (cyclohexyl) | m.p., 148.5° C. |

EXAMPLE 3

Production of the nitroaniline (V)

2-Fluoro-4-nitro-5-(2-propynyl)aminoacetanilide (3.03 g) was suspended in a mixture of ethanol (9.4 ml) and conc. hydrochloric acid (2.7 ml), followed by heating under reflux for 2 hours. After removal of ethanol and conc. hydrochloric acid under reduced pressure, water was added thereto, followed by neutralization with an aqueous sodium bicarbonate solution. The resultant solution was extracted with ethyl acetate, and the extract was washed with water, dried and concentrated to give 2-fluoro-4-nitro-5-(2-propynyl)aminoaniline (1.41 g). m.p., 189°–190° C.

In the same manner as above, the nitroanilines (V) as shown in Table 3 could be obtained.

TABLE 3

(V)

| R | Physical property |
|---|---|
| —CH$_2$(CH$_3$)$_2$ | m.p., 121–122° C. |
| —CH$_2$CH$_2$CH$_3$ | m.p., 114–115° C. |
| —CH$_2$CH=CH$_2$ | m.p., 111.2° C. |
| —CH$_2$C≡CH | m.p., 189–190° C. |
| —⟨H⟩ (cyclohexyl) | m.p., 139.1° C. |

EXAMPLE 4

Production of the nitrobenzene (VI)

A mixture of 2-fluoro-4-nitro-5-(2-propynylamino)aniline (1.41 g) and 3,4,5,6-tetrahydrophthalic anhydride (1.33 g) was suspended in acetic acid (7 ml), followed by heating under reflux for 4 hours. The reaction mixture was cooled, water was added thereto, and the resultant mixture was extracted with ethyl acetate. The extract was washed with water and an aqueous sodium bicarbonate solution, dried and concentrated to give 2-[2-fluoro-4-nitro-5-(2-propynylamino)phenyl]-4,5,6,7-tetrahydro-2H-isoindole-1,3-dione (0.85 g). m.p., 183.5° C.

In the same manner as above, the nitrobenzenes (VI) as shown in Table 4 could be obtained.

TABLE 4

(VI)

| R | Physical property |
|---|---|
| —CH$_2$(CH$_3$)$_2$ | m.p., 139–141° C. |
| —CH$_2$CH$_2$CH$_3$ | m.p., 158–160° C. |
| —CH$_2$CH=CH$_2$ | m.p., 143–145° C. |
| —CH$_2$C≡CH | m.p., 183.5° C. |
| —⟨H⟩ (cyclohexyl) | glassy |

EXAMPLE 5

Production of the aniline (II)

Iron powder (1.22 g) was suspended in a 5% aqueous acetic acid solution, followed by heating at 80° C. A solution of 2-[2-fluoro-4-nitro-5-(2-propynyl)aminophenyl]-4,5,6,7-tetrahydro-2H-isoindole-1,3-dione (0.75 g) in a mixture of acetic acid (2.2 ml) and ethyl acetate (2.2 ml) was dropwise added to the suspension, and the resultant mixture was heated at 70° C. for 3 hours. After removal of the precipitate by filtration, the filtrate was extracted with ethyl acetate. The extract was washed with water and an aqueous sodium bicarbonate solution, dried and concentrated to give 2-[4-amino-2-fluoro-5-(2-propynyl)aminophenyl]-4,5,6,7-tetrahydro-2H-isoindole-1,3-dione (0.59 g). m.p., 182.2° C.

In the same manner as above, the anilines (II) as shown in Table 5 could be produced.

TABLE 5

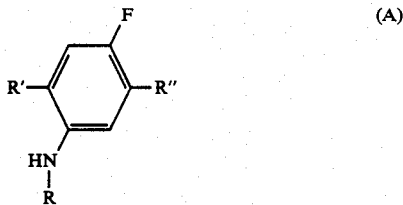

| R | Physical property |
|---|---|
| —CH$_2$(CH$_3$)$_2$ | m.p., 41–43° C. |
| —CH$_2$CH$_2$CH$_3$ | m.p., 185–186° C. |
| —CH$_2$CH=CH$_2$ | m.p., 148–150° C. |
| —CH$_2$C≡CH | m.p., 182.2° C. |
| —⟨H⟩ (cyclohexyl) | glassy |

The above prepared intermediates, i.e. the aminoacetanilide (IV), the nitroaniline (V), the nitrobenzene (VI) and the aniline (II), are novel and can be represented by the general formula:

$$\text{(A)}$$

wherein R is as defined above, R' is an amino group or a nitro group and R" is an amino group, an acetamino group or a 4,5,6,7-tetrahydrophthalimido group, provided that when R' is an amino group, R" is a 4,5,6,7-tetrahydrophthalimido group. These intermediates are also within the scope of the present invention.

In the practical use of the benzotriazoles (I), they may be applied in conventional preparation forms such as emulsifiable concentrates, wettable powders, suspensions and granules in combination with conventional solid or liquid carriers or diluents as well as surface active agents or auxiliary agents. The content of the benzotriazoles (I) as the active ingredient in such preparation forms is usually within a range of 0.05 to 90% by weight, preferably of 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one in Table 1.

FORMULATION EXAMPLE 1

Fifty parts of Compound No. 4, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 1, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

FORMULATION EXAMPLE 3

Two parts of Compound No. 2, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 3 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The benzotriazoles (I) thus formulated in any suitable formulation form are useful for the pre-emergence or post emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzotriazoles (I) over the top of the plants. It may also be applied directly to the weeds if care is taken to keep the chemical off the crop foliage.

The benzotriazoles (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the benzotriazoles (I) can be used as herbicides applicable to agricultural plowed fields as well as paddy fields. They are also useful as herbicides to be employed for orchards, pasture lands, lawns, forests, nonagricultural fields, etc.

The dosage rate of the benzotriazoles (I) may vary on prevailing weather conditions, formulation used, prevailing season, mode of application, soil involved, crop and weed species, etc. Generally, however, the dosage rate is from 0.02 to 100 grams, preferably from 0.05 to 50 grams, of the active ingredient per are. The herbicidal composition of the present invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the benzotriazoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 6 below were used for comparison.

TABLE 6

| Compound No. | Chemical structure | Remarks |
| --- | --- | --- |
| A | [cyclohexyl-benzotriazole-NO2 structure] | U.S. Pat. No. 4,240,822 |
| B | [cyclohexyl-benzotriazole structure] | U.S. Pat. No. 4,240,822 |
| C | [2,4-dichlorophenyl-4-nitrophenyl ether structure] | Commercially available herbicide; "nitrofen" |

TEST EXAMPLE 1

Cylindrical plastic pots (diameter, 10 cm; height, 10 cm) were filled with upland field soil, and the seeds of Japanese millet, redroot pigweed, tall morningglory and velvetleaf were sowed therein and covered with soil. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 7.

TABLE 7

| | | Herbicidal activity | | | |
| --- | --- | --- | --- | --- | --- |
| Compound No. | Dosage (g/are) | Japanese millet | Redroot pigweed | Tall morning-glory | Velvet-leaf |
| 1 | 40 | 5 | 5 | 5 | 5 |
|   | 10 | 4 | 5 | 4 | 5 |
| 3 | 40 | 5 | 5 | 5 | 5 |
|   | 10 | 5 | 5 | 4 | 5 |
| 4 | 40 | 5 | 5 | 5 | 5 |
|   | 10 | 5 | 5 | 4 | 5 |
| B | 40 | 0 | 2 | 0 | 0 |
|   | 10 | 0 | 0 | 0 | 0 |
| C | 40 | 3 | 3 | 2 | 4 |
|   | 10 | 0 | 1 | 0 | 1 |

TEST EXAMPLE 2

Cylindrical plastic pots (diameter, 10 cm; height, 10 cm) were filled with upland field soil, and the seeds of Japanese millet, oats, radish and velvetleaf were sowed therein and cultivated in a greenhouse for 10 days. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined.

The results are shown in Table 8.

TABLE 8

| | | Herbicidal activity | | | |
| --- | --- | --- | --- | --- | --- |
| Compound No. | Dosage (g/are) | Japanese millet | Oats | Radish | Velvet-leaf |
| 1 | 10 | 5 | 5 | 5 | 5 |
|   | 2.5 | 5 | 4 | 5 | 5 |
| 3 | 10 | 5 | 5 | 5 | 5 |
|   | 2.5 | 3 | 3 | 4 | 5 |
| 4 | 10 | 5 | 4 | 5 | 5 |
|   | 2.5 | 4 | 3 | 5 | 5 |
| B | 10 | 0 | 0 | 0 | 0 |
|   | 2.5 | 0 | 0 | 0 | 0 |
| C | 10 | 3 | 2 | 0 | 3 |
|   | 2.5 | 0 | 0 | 0 | 1 |

TEST EXAMPLE 3

Wagner's pots (1/5000 are) were filled with paddy field soil, and the seeds of barnyardgrass (*Echinochloa oryzicola*), broad-leaved weeds (i.e. common falsepimpernel, toothcup, waterwort) and the statoblast of needle spikerush were sowed in 1 to 2 cm depth. Water was poured therein to make a flooded condition. Buds of arrowhead were sowed in 1 to 2 cm depth, and rice seedlings of the 3-leaf stage were transplanted therein, and the test plants were grown in a greenhouse. Five days (at that time weeds began to germinate) thereafter, a designated amount of the test compound formulated in an emulsifiable concentrate according to Formulation Examle 2 and diluted with water (10 ml) was applied to the pots by perfusion, and water was flooded in 4 cm depth. The test plants were grown for an additional 14 days in the greenhouse, and the herbicidal activity was examined. For two days from the treatment, water was leaked with a 3 cm depth per day. The results are shown in Table 9.

TABLE 9

| Compound No. | Dosage (g/are) | Rice plant | Barnyard grass | Broadleaved weed | Needle spikerush | Arrow head |
|---|---|---|---|---|---|---|
| 1 | 1.2 | 2 | 5 | 5 | 5 | 5 |
|   | 0.3 | 0 | 4 | 5 | 5 | 5 |
| 2 | 1.2 | 0 | 5 | 5 | 5 | 4 |
|   | 0.3 | 0 | 4 | 5 | 5 | — |
| A | 1.2 | 0 | 0 | 0 | 0 | 0 |
|   | 0.3 | 0 | 0 | 0 | 0 | 0 |
| B | 1.2 | 0 | 0 | 0 | 0 | 0 |
|   | 0.3 | 0 | 0 | 0 | 0 | 0 |
| C | 1.2 | 0 | 0 | 1 | 1 | 0 |
|   | 0.3 | 0 | 0 | 0 | 0 | 0 |

TEST EXAMPLE 4

Vats (33 cm×23 cm×22 cm) were filled with upland field soil, and the seeds of soybean, corn, wheat, tall morningglory, velvetleaf, prickly sida, common lambsquarters, sicklepod, johnsongrass and green foxtail were sowed therein to 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined.

The results are shown in Table 10.

TEST EXAMPLE 5

Vats (33 cm×23 cm×11 cm) were filled with upland field soil, and the seeds of corn, wheat, rice plant, tall morningglory, common cocklebur, sicklepod, velvetleaf, hemp sesbania and wild mustard were sowed therein and cultivated for 18 days in a greenhouse. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species.

The results are shown in Table 11.

TABLE 11

| Compound No. | Dosage (g/are) | Corn | Wheat | Rice plant | Tall morningglory | Common cocklebur | Sicklepod | Velvetleaf | Hemp sesbania | Wild mustard |
|---|---|---|---|---|---|---|---|---|---|---|
| 1 | 0.63 | 1 | 1 | — | 5 | 5 | 4 | 5 | 5 | 5 |
|   | 0.16 | 1 | 0 | 1 | 4 | 4 | 4 | 5 | — | — |
| 4 | 0.63 | 2 | 1 | 1 | 5 | 5 | 4 | 5 | 5 | 4 |
|   | 0.16 | 1 | 1 | 1 | 4 | 4 | 3 | 4 | — | — |
| A | 0.63 | 0 | 0 | 0 | 0 | 0 | 0 | 1 | 1 | 1 |
|   | 0.16 | 0 | 0 | 0 | 0 | 0 | 0 | 0 | — | — |
| B | 0.63 | 0 | 0 | 0 | 0 | 0 | 0 | 0 | 0 | 0 |
|   | 0.16 | 0 | 0 | 0 | 0 | 0 | 0 | 0 | 0 | 0 |
| C | 0.63 | 0 | 0 | 0 | 0 | 0 | 0 | 0 | 0 | 0 |
|   | 0.16 | 0 | 0 | 0 | 0 | 0 | 0 | 0 | 0 | 0 |

What is claimed is:
1. A compound of the formula:

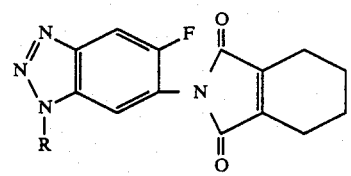

wherein R is a $C_1$–$C_5$ alkyl group, a $C_3$–$C_5$ alkenyl group, a $C_3$–$C_5$ alkynyl group or a $C_3$–$C_7$ cycloalkyl group.

2. The compound according to claim 1, wherein R is a $C_3$–$C_5$ alkenyl group.

3. The compound according to claim 1, wherein R is a $C_3$–$C_5$ alkynyl group.

TABLE 10

| Compound No. | Dosage (g/are) | Soybean | Corn | Wheat | Tall morningglory | Velvetleaf | Prickly sida | Common lambsquarters | Sicklepod | Johnsongrass | Green foxtail |
|---|---|---|---|---|---|---|---|---|---|---|---|
| 3 | 10 | 0 | — | — | 5 | 5 | 5 | 5 | 4 | 5 | 5 |
|   | 2.5 | 0 | — | 0 | 4 | 5 | 4 | 5 | 3 | 4 | 4 |
| 4 | 10 | 1 | 1 | — | 5 | 5 | 5 | 5 | 4 | 5 | 5 |
|   | 2.5 | 0 | 0 | 1 | — | 4 | 4 | 5 | 3 | 4 | 4 |
| A | 10 | 0 | 0 | 0 | 0 | 2 | 1 | 2 | 0 | 3 | 3 |
|   | 2.5 | 0 | 0 | 0 | 0 | 0 | 0 | 1 | 0 | 1 | 0 |
| B | 10 | 0 | 0 | 0 | 0 | 0 | 0 | 0 | 0 | 0 | 0 |
|   | 2.5 | 0 | 0 | 0 | 0 | 0 | 0 | 0 | 0 | 0 | 0 |
| C | 10 | 0 | 0 | 0 | 0 | 0 | 0 | 0 | 0 | 0 | 0 |
|   | 2.5 | 0 | 0 | 0 | 0 | 0 | 0 | 0 | 0 | 0 | 0 |

4. The compound according to claim 2, wherein the $C_3-C_5$ alkynyl group is a member selected from the group consisting of allyl, crotyl, and methallyl.

5. The compound according to claim 3, wherein the $C_3-C_5$ alkynyl group is a member selected from the group consisting of propargyl, 2-butynyl, 3-butynyl, 2-pentynyl, and 3-pentynyl.

6. The compound according to claim 1, wherein the $C_1-C_5$ alkyl group is a member selected from the group consisting of methyl, ethyl, n-propyl, isopropyl, n-butyl, isobutyl, sec-butyl, and n-pentyl.

7. The compound according to claim 1, wherein the $C_3-C_7$ cycloalkyl group is a member selected from the group consisting of cyclopropyl, cyclobutyl, cyclopentyl, cyclohexyl, and cycloheptyl.

8. The compound according to claim 1, which is 2-[5-fluoro-1-(2-propynyl)benzotriazol-6-yl]-4,5,6,7-tetrahydro-2H-isoindole-1,3-dione.

9. The compound according to claim 1, which is 2-[5-fluoro-1-(2-propenyl)benzotriazol-6-yl]-4,5,6,7-tetrahydro-2H-isoindole-1,3-dione.

10. A herbicidal composition which comprises as an active ingredient a herbicidally effective amount of the compound according to claim 1, and an inert carrier or diluent.

11. A method for controlling weeds which comprises applying a herbicidally effective amount of the compound according to claim 1 to an area where weeds grow or will grow.

* * * * *